US007906131B2

(12) United States Patent
Brower

(10) Patent No.: US 7,906,131 B2

(45) Date of Patent: Mar. 15, 2011

(54) FORMULATION AND METHOD FOR TREATING PLANTS TO CONTROL OR SUPPRESS A PLANT PATHOGEN

(75) Inventor: William Brower, Fortville, IN (US)

(73) Assignee: William Brower, Fortville, IN (US)

( * ) Notice: Subject to any disclaimer, the term of this patent is extended or adjusted under 35 U.S.C. 154(b) by 862 days.

(21) Appl. No.: 11/622,629

(22) Filed: Jan. 12, 2007

(65) Prior Publication Data

US 2007/0110725 A1 May 17, 2007

Related U.S. Application Data

(63) Continuation of application No. PCT/US2005/025012, filed on Jul. 13, 2005.

(60) Provisional application No. 60/587,563, filed on Jul. 13, 2004.

(51) Int. Cl.

| | |
|---|---|
| ***A01N 25/00*** | (2006.01) |
| ***A01N 63/00*** | (2006.01) |
| ***C12N 1/12*** | (2006.01) |
| ***C12N 1/20*** | (2006.01) |
| ***C12P 1/00*** | (2006.01) |
| ***C12S 3/00*** | (2006.01) |

(52) U.S. Cl. .................... 424/405; 424/93.4; 424/93.46; 424/93.461; 424/93.462; 424/93.47; 435/252.1; 435/252.4; 435/252.5; 435/253.3; 435/267; 435/822; 435/831; 435/836; 435/837; 435/839; 435/876

(58) Field of Classification Search ........................ None
See application file for complete search history.

(56) References Cited

U.S. PATENT DOCUMENTS

| | | | | |
|---|---|---|---|---|
| 4,975,105 | A * | 12/1990 | Kremer et al. | 71/6 |
| 5,639,794 | A * | 6/1997 | Emerson et al. | 514/699 |
| 6,471,741 | B1 * | 10/2002 | Reinbergen | 71/6 |
| 6,602,500 | B1 * | 8/2003 | Kharbanda et al. | 424/93.46 |
| 6,649,566 | B2 * | 11/2003 | Doostdar | 504/140 |
| 2003/0068303 | A1 * | 4/2003 | Selvig et al. | 424/93.1 |
| 2003/0082792 | A1 * | 5/2003 | Bergstrom et al. | 435/252.5 |

* cited by examiner

*Primary Examiner* — Deborah K. Ware

(74) *Attorney, Agent, or Firm* — Woodard Emhardt Moriarty McNett & Henry, LLP

(57) ABSTRACT

The present invention provides formulations and methods for controlling or suppressing bacterial or fungal plant pathogens, including *Erwina amylovora* the bacteria that causes fire blight. A formulation for controlling of suppressing a plant pathogen may include at least one beneficial species of bacteria, at least one beneficial species of fungi, a nutrient, at least one compound that extends the length of time that the formulation remains effective. Typically the formulation is applied to the above ground structures of the plant including its leaves, flowers, stems, trunk, blossoms and fruit.

6 Claims, 6 Drawing Sheets

FORMULATION AND METHOD FOR TREATING PLANTS TO CONTROL OR SUPPRESS A PLANT PATHOGEN

CROSS REFERENCE TO RELATED APPLICATIONS

This application is a continuation of International Patent Application Ser. No. PCT/US2005/025012 filed Jul. 13, 2005, which claims the benefit of U.S. Provisional Patent Application Ser. No. 60/587,563 filed on Jul. 13, 2004, both of which are hereby incorporated by reference in their entirety.

BACKGROUND OF THE INVENTION

This invention relates to formulations and methods for controlling and suppressing plant pathogens.

Plants including many commercially valuable cultivars ranging from fruit trees and crop plants to ornamental shrubs are affected by pathogens including a wide spectrum of bacterial and fungal pathogens. Taken together bacterial and fungal infestations have a huge economic impact on commercial agriculture. Many pathogenic microorganisms are spread by insect activity consequently much damage attributable to insect infestations is in fact caused by microorganisms which insects spread from infected to uninfected plants. Another common pathway for the spread of infection is wind or rain. Accordingly, a great deal of time and expense is devoted to trying to protect plants from these pathogens or to minimize the damage they do once they infect a given plant.

Bacterial pathogens which do significant damage to cultivated plants, include, for example, *Xanthomonas campestric*, which causes leaf blight, and *X. campestric* (which causes Walnut blight). One particularly devastating bacterial pathogen is fire blight caused by the bacterium *Erwinia amylovora* this bacteria is related microorganisms which cause soft rot diseases such as *E. carotovora* and *E. chrysanthemi*, and species of *E. Pantoea* such as *stewartii* which causes Stewarts wilt in corn and hervicola. Fire blight infection is characterized by wilting and tissue necrosis. Fire blight itself affects many varieties of commercially important pome fruit trees, many varieties of apple and pear trees are particularly susceptible to fire blight. Other susceptible species include various varieties of stone fruit trees and some ornamental plants.

Affected areas of plants with fire blight appear scorched and blackened, symptoms which give fire blight its common name. Symptoms vary with the susceptibility of the plant and environmental conditions. Effects range from the destruction of specific plant structures to the death of the entire plant. For a more detailed discussion of fire blight the reader is directed to an article by J. A. Eastgate, *Molecular Plant Pathology* (2000) 1 (6), 325-329 and references therein.

The microorganism which causes fire blight generally enters a susceptible plant through one of five primary routes for infestation these include: formation of a canker; through a blossom; through new root or shoot tissue; or in response to trauma damage caused by storms or by human or animal activity. One common pathway to infection is through overwintering of the organism in the bark of trees or in a canker on or in the bark. Cankers can be small and are easily overlooked during the winter pruning efforts. During the spring, the pathogen may ooze from the canker in a sticky, sap-like liquid which is readily dispersed by rain, wind, and pollinating insects such as bees. Once dispersed the pathogen may infect blossoms of the same or neighboring plants. Infection of the blossoms is commonly referred to as blossom blight.

Blossom blight represents one particularly devastating form of the infection. Once the first infected stamen appears, pollinators, wind and rain can rapidly carry the pathogen from one bloom to another. An entire orchard can be colonized within a several hours or few days; when environmental conditions are suitable, the pathogen population can double within 20 to 30 minutes. Consequently, fire blight has been known to spread exponentially through stands of susceptible plants. When conditions favor the pathogen it may sweep across an entire apple or pear tree orchard in a matter of only two to three days.

Once fire blight has infected a portion of a plant, growers must act aggressively to isolate the infected portion or in some cases the entire plant. Failure to take the appropriate remedial action immediately may result in loss of the entire orchard or surrounding nurseries. The most common approach to trying to control an outbreak of fire blight is to aggressively prune and in some cases completely destroy the infected plants. It is also common practice to destroy nearby non-infected plants in order to reduce the risk that the infection may spread into the entire orchard.

Additional approaches to fire blight control include treating plants with copper salts and antibiotics such as streptomycin and/or tetracycline. Since treatment after infestation is not always effective, nurseries often resort to prophylactically treating entire orchards with antibiotics to try and reduce the susceptibility of their crops to fire blight. As a result there have been reports of increased amounts of antibiotic residues in fruits, insects, and the soil around some orchards treated for fire blight. Furthermore, the widespread use of antibiotics has helped to select for variants of *E. amylovara* that are resistance to the antibiotics commonly used against *E. amylovora*. Despite these efforts, epidemics of fire blight appear to explode in orchards, many of which have no known history of infestation with fire blight. Clearly then, currently used methodologies for the control of fire blight are not particularly effective.

Equally devastating to various commercially important crops are infestations caused by fungal plant pathogens. Fungal pathogens of considerable economic impact include, but are in no ways limited to: *Venturia inaequalis*, which causes Apple Scab; *Gnomonia setecea* which causes Birch Blight; *Mycosphaerella populorum*, which causes *Septoria* (Leaf Spot) in Dogwood trees; *Gymnosporangium globosum*, which affects Hawthorn trees and shrubs; and *Kabatina juniperii*, which cause a from of Juniper Blight. Because the fungal infestations are difficult to treat, growers often take prophylactic action to reduce the risk for infection. Prophylactic activities include pruning, isolating and oftentimes destroying trees or other plants infected with fungal pathogens. Other approaches currently available include the application of chemical and biological fungicides. These approaches are often expensive and they are not always wholly effective in suppressing the infestation or controlling the economic damage done by fungal plant pathogens.

There is a need then for effective, economical formulations and methods for the control and suppression of plant pathogens including those caused by pathogenic bacteria and fungi.

BRIEF SUMMARY

Figure 1:
FIG. 1 is a scanned image of trees infected with fire blight.
Figure 2:
FIG. 2 is a scanned image of leaves from a tree infected with fire blight.
Figure 3:
FIG. 3 is a scanned image of a tree, which had been infected with fire blight and sprayed to try and control the infection.
Figure 4:
FIG. 4 is a scanned image of a plant that was infected with fire blight and has been sprayed at least twice using a formulation for controlling fire blight.

One aspect relates to a formulation for the suppression or control of plant pathogens including, but not limited to, bacterial pathogens such *Erwinia amylovora* the bacterial which causes fire blight, and fungal pathogens such as: *Venturia inaequalis*, which causes Apple Scab; Gnomonia setecea which causes Birch Blight; *Mycosphaerella populorum*, which causes *Septoria* (Leaf Spot) in Dogwood trees; *Gymnosporangium globosum*, which affects Hawthorn trees and shrubs; and *Kabatina juniperii*, which cause a form of Juniper Blight.

Various aspects are novel, nonobvious, and provide various advantages. While the actual nature of the invention covered herein can only be determined with reference to the claims appended hereto, certain forms and features, which are characteristic of the preferred embodiments disclosed herein, are described briefly as follows.

One embodiment is a formulation for controlling or suppressing plant pathogens which includes beneficial bacteria, and fungi, as well as nutrients beneficial to the microorganisms and/or plant. These materials are selected for their ability to help control and/or eliminate plant pathogens including for example, bacterial and fungal pathogens which affect plants. In one embodiment the formulation is applied to the above ground surfaces of infected or susceptible plants to prevent, or control infections caused by plant pathogens such as *E. amylovora.*

In still another embodiment the formulation includes additional components that aid in the control of at least one plant pathogen including, for example, nutrients, surfactants, vitamins, minerals, leaf stickers, wetting agents and the like. Suitable sticking agents include, but are not limited to aluminum silicate, Kaolin clay, yacca plant extract, and the like.

In another embodiment the formulation includes compounds that promote the efficacy of the formulation including, but not limited to, compounds that protect at least one component of the formulation from UV light and/or from rapid desiccation and/or by helping to form a microenvironment favorable to the plant and beneficial microorganism.

Still another embodiment includes wetting agents that help to disperse the formulation into aqueous preparations and may aid in spreading the formulation onto the surfaces of above ground plant structures.

In still another embodiment the formulation may include a variety of other materials advantageous to plant health such as pesticides, insecticides, biocides, fungicides and the like.

Another aspect provides a formulation and method for controlling or suppressing infection by plant pathogens or to reduce the amount of damage done to a planted area by an outbreak of a particular plant pathogen. Theses methods include spraying or drenching plants with a formulation for the control or suppression of plant pathogens such as pathogenic bacteria and/or fungi. The formulation may include one or more of beneficial bacterial and fungi, nutrients and other ingredients that increase the health of the plant and/or beneficial microorganisms. The formulation may further include compounds that promote the efficacy of the formulation including, but not limited to, compounds that protect at least one component of the formulation from UV light or desiccations or wetting agents that help to disperse the formulation into aqueous preparations and may aid in spreading the formulation onto above ground plant structures.

One embodiment provides a formulation for controlling or suppressing plants pathogens, comprising: a set of microorganisms including at least one beneficial bacteria; at least one beneficial fungi; at least one nutrient useful to either or both the plant and at least one beneficial microorganisms; and at least one compound which extends the effective life time of the formulation.

In one embodiment the formulation for the control or suppression of plant pathogens includes at least one beneficial bacteria selected from the group consisting of: *Bacillus subtilis, Baccillus licheniformis, Bacillus axotoformans, Bacillus megaterium, Bacillus coagulans, Bacillus pumulis, Bacillus thurengiensis, Bacillus stearotermophilis, Paenbacillius polymyxa, Paenibaccillus durum, Azotobacter chroococcum, Azotobacter vinleandii, Sacchromyces cervisiae, Streptomyces lydicus, Pseudomonas aureofaceans* and *Pseudomonas fluorescens.*

In one embodiment the formulation for the control or suppression of plant pathogens includes at least one fungi selected from the group consisting of: *Laccaria bicolor, Laccaria butilus, Laccaria laccata, Paenibacillus polymyxa, Paenibacillus durum, Pisolitus tinctorius, Rhizopogon ellanae, Rhizopogon rubescens, Rhizopogon subscaerlescens, Rhizopogon vulgari, scleroderma cepa, scleroderma citrium.*

In one embodiment the formulation for the control or suppression of plant pathogens includes at least one microorganism selected from the group consisting of *Trichoderma harzianum* and *Trichoderma konigii.*

In one embodiment the formulation for the control or suppression of plant pathogens includes at least one species of beneficial yeast such as, for example, *Saccharomyces cervisiae.*

In one embodiment the formulation for the control or suppression of plant pathogens includes at least one nutrient selected from the group consisting of: sea kelp extract, yucca plant extract, maltodextrin, dextrose, inactive yeast, calcium salt, humic acid, vitamin A, vitamin E, biotin, folic acid, vitamin B, vitamin B2, vitamin B3, vitamin B6, vitamin B7, vitamin B12, vitamin C, vitamin K, ammonia, phosphate, iron, calcium glucoheptonate, zinc, trace metals and other minerals commonly found in preparations such as some forms of clay and the like.

In one embodiment the formulation for the control or suppression of plant pathogens is in a form suitable for application to the above ground structures of plants. Above ground plant structures which can be drenched or sprayed with the formulation include, but are not limited to, a plant's stem, leaves, shoots, stalks, trunk, bark, petioles, fruiting bodies, fruits, flowers, buds and the like.

In one embodiment the formulation for the control or suppression of plant pathogens includes at least one sticking agent. A sticking agent is a compound that increases the length of time that at least one other component in the formation stays in contact with another component of the formulation and/or with a surface of the plant. Suitable sticking agents include, but are not limited to, yacca plant extract, and clays such as Kaolin clay, fine benign hygroscopic powders and the like.

In one embodiment the formulation for the control or suppression of plant pathogens includes at least one compound that extends the time period over which the formulation remains effective. Compounds for extending the effective period of a formulation includes at least one compound selected from the group consisting of aluminum silicate, fine clays, Kaolin clay, aluminum oxide, zinc oxide, and the like.

In one embodiment a formulation for the control or suppression of a plant pathogen is dispersed in an aqueous preparation. The aqueous preparation may include between about 1.5 to about 12 pounds of fine clay, for example, Kaolin clay, per 100 gallons of aqueous preparation.

Another aspect is a method for controlling or suppressing plant pathogens which includes the steps of providing an aqueous formulation and applying the aqueous preparation to plants. The amount of the preparation applied to a given field or stand of plants can be expressed as the number of gallons of a standard preparation of the formulation applied per acre of planted area. The aqueous preparation on a one hundred gallon basis may include between about $1.0\times10^8$ and $2.0\times10^8$ cfu at of least one beneficial bacteria selected from the group consisting of *Bacillus subtilis, Bacillus axotoformans, Bacillus megaterium, Bacillus coagulans, Bacillus pumulis, Bacillus thurengiensis, Bacillus stearotermophilis, Baccillus licheniformis, Paenbacillius polymyxa, Paenibaccillus durum, Azotobacter chroococcum, Azotobacter vinleandii, Streptomyces lydicus, Pseudomonas aureofaceans and Pseudomonas fluorescens*; between about $1.0\times10^7$ to about $20.0\times10^7$ cfu of at least one beneficial fungi selected from the group consisting of *Rhizopogon rubescens, Rhizopogon vulgaris, Rhizopogon subscaerlescens, Rhizopongon ellanae, Pisolithus tinctorius, Laccaria laccata* and *Laccaria bicolor, Scleroderma cepa, S. citrinum*; between about $1.0\times10^8$ and about $2.0\times10^8$ cfu of *Saccromyces cervisiae*; between about 1.2 to about 12 pounds of aluminum silicate or Kaolin clay; between about 20 to about 100 grams of yeast extract; between about 20 to about 100 grams of calcium glucoheptonate; between about 20 to about 100 grams of yacca plant extract, and between about 100 grams to about 500 grams of sea kelp.

In one embodiment the aqueous preparation is applied in the amount of between 15 gallons to about 350 gallons per acre of area including the plants of interest.

In one embodiment a formulation not intended for treatment of certain plants that produce edible fruits or other edible structures may include, between about $2.5\times10^7$ cfu to about $5.0\times10^7$ cfu of at least one strain of *Tricoderma* selected form the group consisting of *T. harzianum* and *T. konigii* and between about $1.0\times10^8$ to about $2.0\times10^8$ cfu *Baccillus licheniformis* per one hundred gallons of an aqueous preparation.

Further objects, features, aspects, forms, advantages and benefits shall become apparent from the description and drawings contained herein.

DETAILED DESCRIPTION OF THE INVENTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

Suppression or suppressing—generally refers to preventing a disease or pathogen from infecting or affecting a given plant or group of plants. When these terms are used herein no claim is made as to the actual mechanism of suppression, for example, a given suppressor may be acting as a biocide, bactericide, bacteriostat, fungicide, fungistat, insecticide, or it may interfere with one or more functions of a given pathogen that enables the pahtogen to infect a given plant under a given set of environmental conditions, or by any other mechanism. All that is to be inferred by use of the terms suppression or suppressing is that a given formulation appears to prevent a plant from becoming symptomatic for infection or assault by at least one plant pathogen.

Control or Controlling—generally refers to limiting the economic damage done to a given plant or group of plants by limiting the damage done to the plants by at least one plant pathogen. When this term is used herein no claim is made as to the actual mechanism of pathogen control, for example, a given formulation may act to control a pathogen by acting as a bactericide, bacteriostat, fungicide, fungistat, insecticide, or by interfering with one or more functions of a given pathogen that enables the pathogen to infect a given plant under a given set of environmental conditions, or by any other mechanism. All that is to be inferred by use of the terms control or controlling is that a given formulation appears to reduce the amount of damage done by a plant pathogen to a given plant relative to a similarly situated plant that is likewise infected with the pathogen, but not exposed to the formulation.

The present invention provides formulations and methodologies for controlling or suppressing plant pathogens including, but not necessarily limited to, pathogenic bacteria and fungi. The group of plant pathogens that can be controlled using formulations made in accordance with various embodiments include, but are not limited to *Erwinia amylovora* the bacteria, which causes fire blight and the fungus *Venturia inaequalis*, which causes Apple Scab.

The formulations according to various embodiments may include at least one beneficial bacteria species. Beneficial bacteria are bacteria which favorably impact the health of a given plant under a given set of environmental conditions or in response to given realized or potential threat to the health of the plant. Beneficial bacteria, positively impact plant health by a variety of mechanism including, but not limited to: occupying a growth space otherwise occupied by a pathogen; creating a micro-environment which disfavors the colonization, growth or development of at least one plant pathogen; providing at least one compound that is usefully to the health of the plant; providing an increase in the uptake of plant nutrients and minerals; binding to receptors on the surface to the plant that would otherwise be occupied by at least one plant pathogen; directly or indirectly contributing to the well being of other beneficial organisms; and any combination of the aforementioned mechanisms.

Examples of beneficial bacteria include, but are not limited to *Azotobacter chroococcum, Azotobacter vinleandii, Bacillus azotoformans, Bacillus coagulans, Bacillus megaterium, Bacillus polymyxa, Bacillus pumilis, Bacillus sterotermophilis, Bacillus subtilis, Bacillus thuringiensis, Paenibacillus polymyxa, Paenibacillus durum, Paenibacillus asotobixans, Pseudomonas aureofaceans, Pseudomonas fluorescens, Pseudomonas monteilii, Streptomyces lydicus, Streptomyces griseoviridis*, and mixtures thereof.

The formulations according to various embodiments may include at least one beneficial fungal species. Beneficial fungi are fungi which favorably impact the health of a given plant under a given set of environmental conditions or in response to given realized or potential threat to plant health. Beneficial fungi, positively impact plant health by a variety of mechanism including, but not limited to: occupying a growth space otherwise occupied by a potential pathogen; creating a micro-environment which disfavors the colonization, growth or development of at least one plant pathogen; providing at least one compound that is usefully to the health of the plant; providing an increase in the uptake of plant nutrients and minerals; binding to receptors on the surface to the plant that would otherwise be occupied by at least one plant pathogen; directly or indirectly contributing to the well being of other beneficial organisms; and any combination of the aforementioned mechanisms.

Examples of beneficial fungi include, but are not limited to *Laccaria bicolor, Laccaria butilus, Laccaria laccata, Paenibacillus polymyxa, Paenibacillus durum, Pisolitus tinctorius, Rhizopongon ellanae, Rhizopogon rubescens, Rhizopogon subscaerlescens, Rhzopogon vulgaris, Scleroderma cepa* and *S. citrinum.*

Embodiment not intended for use on certain fruit tress and crop plants may also include the beneficial microorganisms *Trichoderma harzianum, Trichoderma konigii*, and *Bacillus licheniformis.*

Additional beneficial microorganisms may include for example, the yeast *Saccharomyces cervisiae.*

The formulations according to various embodiments may also include at least one microorganism that is involved in nutrient cycling. Nutrients cycled by a given microorganism may benefit a plant by, for example, directly supply the plant with at least one useful compound, or by supplying other useful microorganisms in the microenvironment with at least one necessary or useful compound. Additional benefits from nutrient recycling may include replenishing at least one compound that adversely affects the health or survival of at least one plant pathogen. It is to be understood that a given microorganisms may simultaneously perform more than one of the aforementioned functions in a given microenvironment.

The formulations according to various embodiments may include at least one nutrient that is beneficial to the plant or to at least one beneficial microorganism. Nutrients that may be included in the formulation include, but are not limited to, the following: carbon sources such as simple or complex carbohydrates; sources of nitrogen either elemental such as ammonia or organically bound such as killed bacteria and or inactive yeast or extracts thereof; calcium, for example in the form of calcium glucoheptonate; phosphates; metals such as iron, zinc, and other trace metals; vitamins including, but not limited to vitamin A, B complex, E, folic acid, and vitamins D and E, humic acid; yacca plant (*Yacca schidegera*) extract; and any mixture thereof.

The formulations according to various embodiments may include at least one sticking agent. A sticking agent is a compound that has as at least one its characteristics the ability to adhere to a surface structure of a plant or to at least one other component in a given formulation. Suitable sticking agents include, but are not limited to yacca plant extracts, Kaolin clay; fine wet-able powders, and the like.

The formulations according to various embodiments may include at least one agent or compound that at least helps to protect components of a given formulation from the damaging effects of ultraviolet (UV) radiation, or from rapid desiccation. These compounds include, but are not limited to fine clays, Kaolin clay, aluminum oxide, zinc oxide, aluminum silicate and the like.

The formulations according to various embodiments may include at least one wetting agent. A wetting agent promotes the dispersal of the formulation in an aqueous environment. Wetting agents may also promote a more even, more efficient spreading of various components in the formulation onto above ground plant structures including, but not limited to, leaves, stems, petioles, bark, blossoms, fruits and the like. Suitable wetting agents include, but are not limited to yacca plant extract.

In one embodiment, the method for treating a plant includes a spray or drench application of an aqueous preparations of a formulation for the control or suppression of a plant pathogen to the exposed surfaces of a plant, i.e., any part of the plant extending above ground. This includes the undersides, top, or side surfaces of leaves, stems, trunk bark, buds, blossoms, flowers, fruits and the like, or parts thereof.

Many of the beneficial microorganisms named in the above have been identified as having certain beneficial effects when they are in the soil or when they are associated with the roots of specific plants. Examples of bacteria in the list that are thought to interact at the soil level with various plants include *Bacillus azotoforman*, which is involved in nitrogen fixation; *B. azotoformans*, which affects plant growth; *B. polymyza* which exhibits antifungal activity; *B. thuringiensis* which is entormopathogenic; *B. licheniformis* which acts on the production of plant growth hormones, and *B. pumulis* which is involved in nutrient cycling.

For further discussion of some of these microorganisms the reader is directed to the following references all of which are herein incorporated by reference in their entirety: Timmusk S, Wagner E G., *The plant-growth-promoting rhizobacterium Paenibacillus polymyxa induces changes in Arabidopsis thaliana gene expression: a possible connection between biotic and abiotic stress responses.*, Mol Plant Microbe Interact. 1999 Nov. 12 (11):951-9; Ditengou, F A; Raudaskoski, M; Lapeyrie, F., *Hypaphorine, an indole*-3-*acetic acid antagonist delivered by the ectomycorrhizal fungus Pisolithus tinctorius, induces reorganization of actin and the microtubule cytoskeleton in Eucalyptus globules ssp bicostata root hairs.*, PLANTA. 2003, 218(2):217-225; Shi, L B; Guttenberger, M.; Kottke, I; Hampp, R., *The effect of drought on mycorrhizas of beech* (*Fagus sylvatica L.*): *changes in community structure, and the content of carbohydrates and nitrogen storage bodies of the fungi.*, MYCORRHIZA, 2002, 12(6):303-311; and Jentschke, G., Winter, S., Godbold, D., *Ectomycorrhizas and cadmium toxicity in Norway spruce seedlings.* [online] Abstract page of ICOM II website (Uppsala, Sweden) [retrieved on 2005 Mar. 08]. Retrieved from the Internet:<URL: http://mycorrhiza.ag.utk.edu/latest/icoms/ICOM2/ICOM2_Jentschke.htm.

Most of what is known about these organisms is characterized by how they interact with various plants when they are in the soil or in plant tissue. One embodiment of the invention exploits the ability of at least some of these organisms to beneficially impact plant pathogen suppression and control when the organism are applied to the above ground structures of various plants. The beneficial effects observed by application of some of these organisms to the above ground surfaces of various plants may be enhanced by the additions of various nutrients. Similarly the beneficial effects observed are increased by the addition of relatively small amount of a fine clay compound such as Kaolin clay.

Another embodiment includes a spray or drench application about the locus of the plants including, for example, spraying the ground around the plant, particularly from the trunk or stem out to the drip line and/or injecting an aqueous solution of the control formulation into the ground around or under the plants or near the plant roots.

In one embodiment, an application of a formulation for the control or suppression of a plant pathogen can includes dusting the exposed portions of a plant with a solid or powdered composition comprising the formulation. Still another embodiment includes applying the powdered composition to the ground around the plants or in the ground under the plants.

The spraying primarily of a liquid preparation of the formulation can be accomplished by a variety of methods including, but not limited to, blast sprayers, hose reel and hand gun, walking sprays, aerial sprays and the like.

One embodiment provides formulations for the prophylactic treatment of plants prior to exposure to an infectious agent or after confirmed or suspected exposure but before the plant become symptomatic for an infection. Still another embodiment provides control of a pathogen by applying the formation to plants, which exhibit the symptoms and/or other evidence of infection of bacterial or fungal plant pathogens. Still another embodiment can control an infestation of plant pathogen by reducing the amount of damage done to the plant and by at least slowing the rate at which the infestation spreads to other parts of the host plant.

For suppression of a plant pathogen a prophylactic treatment application can be made before the first signs of infestation or when environmental conditions appear to favor an outbreak.

In one embodiment, the formulation is applied to plants as required and in conformity with all governmental mandates and laws. In one embodiment, aqueous ready-to-use spray formulation is applied prophylactically before the first appearance of flower or in early to full bloom. The prophylactic treatment can be repeated as desired or deemed expedient based upon the environmental conditions and/or the observance of bacterial infestation of neighboring plants, fields or orchards.

One embodiment provides the ability to control and significantly reduce and perhaps eliminate fire blight infestation from an infected plant. Application of a control formulation to an infected plants is not dependent upon whether the plants have been previously treated or the class or identity of the active ingredient that was previously used to try and kill and/or control the infection.

In one embodiment, the application sequence includes at least a first application to the plants at the early flower stage, including for example, the appearance of first stamen to full bloom. The treatment regime can also include at least one additional application as necessary to control an infection or threat of infection. Appropriate additional applications can be made, for example, at about ⅔ flower or within 10 to 14 days of the first application, or longer depending upon the particular formulation used, environmental conditions and overall health and susceptibility of the plants.

One embodiment provides a formulation for the control or suppression of a pathogen that extends the period of time over which the formulation is effective.

In other embodiments, a control formulation is applied no later then about 2 weeks prior to harvesting edible fruit.

In one embodiment a formulation for the control or suppression of a pathogen includes at least one beneficial bacteria species. In still another embodiment a given formulation may include, for example, three, four, five, ten, or more different beneficial bacterial species admixed together along with sufficient nutrients. The formulation includes the beneficial bacteria species in an amount sufficient to control or suppress infestation with a bacterial or fungal pathogen in plants. Formulations intended for above ground use, generally include only ecto mycorrhizal species of fungi.

In one embodiment the formulation can includes between about $1.0\times10^{7}$ cfu and about $1.0\times10^{11}$ cfu of a single beneficial bacterial species per gal. ($2.5\times10^{9}$ cfu/gal.). In another embodiment the ready-to-use formulation includes between about $1.0\times10^{8}$ cfu and about $1.0\times10^{10}$ cfu of a single bacterial species per gal. It will be understood that the ready-to-use formulation can include a number of different bacterial species each included in the above prescribed, approximate amounts.

As with the bacterial species, a given control or suppression formulation can include more than one fungal species, for example, the control formulation may include two, three, four, five or ten or more different species of fungus. The different fungus species can include either endo mycorrhizae or ecto mycorrhizae species, each included fungus species can be included in an amount sufficient to provide at least one beneficial effect to the plant.

In one embodiment, a ready-to-use formulation can contain between about $1.0\times10^{5}$ cfu/gal and about $1.0\times10^{9}$ cfu/gal of a single fungus per gal. ($7.5\times10^{7}$ cfu per gal.). More preferably the ready-to-use formulation can include between about $1.0\times10^{6}$ cfu/gal and about $1.0\times10^{8}$ cfu/gal of a single fungus per gal. It will be understood that the ready-to-use formulation can include a number of different fungi, each included in the above prescribed, preferred amounts.

In one embodiment, the formulation for the control or suppression of a plant pathogen includes a mixture of mycorrhizal and tricoderma species.

In one embodiment the formulation for the control or suppression of a pathogen includes at least one ecto mycorrhizal species in combination with at least one species of *Tricoderma* and at least one species of beneficial bacteria.

In one embodiment the formulation can also include a nutrient. Preferably the nutrient is selected for its ability to enhance the stability, longevity and/or propagation of the beneficial bacteria, fungi, plant structure or root plant. Examples of nutrients for use with the present invention includes, but are not limited to humic acids, sugars, dextrins (particularly maltodextrin), dextrose, and dried yeast, or yeast extract. The nutrients can be added in amounts ranging between about 1 wt % and about 15 wt %, based upon the total weight of the formulation.

The formulation can also include one or more emulsifying agents known to those skilled in the art.

The plant pathogen control or suppression formulation can include a variety of optional additives. Stickers that may be used in some embodiments include, for example, soluble yucca plant extract derived from the *Yucca schidigera*, fine clays and Kaolin clay. The sticker can be combined in amounts up to about 12 wt % of the total weight of a ready to use formulation. Surfactants can be used in the formulation including the anionic, cationic, and/or non-ionic types. Examples of surfactants include but are not limited to: aliphatic sulfonic ester salts like lauryl sulfate, aromatic sulfonic acid salts, salts of lignosulfates, and soaps. Examples of nonionic surfactants are the condensation products of ethylene oxide with fatty alcohols such as oleylalcohol, alkyl phenols, lecithins, and phosphorylated surfactants, such as phosphorylated ethylene oxide/propylene oxide block copolymer and ethoxylated and phosphorylated styryl-substituted phenol. Additional surfactants are anionic wetting agents, such as sodium salts of sulfated alkyl carboxylate, and/or alkyl naphtalenesulphonate, and/or dispersing agents such as naphthalene formaldehyde condensate The formulation can also include a variety of other ingredients such as vitamins and minerals. Examples of vitamins for use in the composition include but are not restricted to the following: biotin, folic acid, vitamins B, B2, B3, B6, B7, B12, C, and K. Examples of minerals include any mineral that can enhance the growth of the plant and/or beneficial bacteria. Specific examples of minerals include: potassium, iron, sulfur, magnesium, boron, manganese, and zinc.

Still other embodiments includes within its scope the dusting or application of a plant pest control formulation or solid mixture that includes at least one beneficial bacteria, one beneficial fungi, nutrients for the beneficial microorganism, and a fine clay such as Kaolin clay, which may extend the useful half-life of the formulation.

In the powdered mixture various carriers or fillers can be added. Examples of carriers or fillers include, but are not limited to, aluminum silicate, aluminum oxide, attaclay, bentonite, bole, calcium carbonate, calcium sulfate, celite, chalk, diatomaceous earth, dolomite, Fuller's earth, gypsum, Kaolin clay, kieselguhr, lime, limestone, magnesia (powdered), magnesium oxide, pyrophyllite, silica gels, silicates, silicic acid, silicium oxide, and/or talc and mixtures thereof.

One embodiment includes within its scope a concentrated formulation for the control or suppression of a plant pathogen. The concentrated formulation can be either a solid (powdered or granulated) mixture or a concentrated, aqueous mixture. The concentrate can include any or all of the above described ingredients. The concentrated formulation may include the ingredients described in the above in amounts of between about 2 to about 10 fold of the amounts specifically described herein. In use, the concentrate can be admixed with water to provide the ready-to-use formulation.

One embodiment provides a method for treating plants including fruiting plants, ornamental plants and deciduous plants to control and halt the spread of bacterial pathogens including, for example, fire blight (*Erwinia amylovora*). One embodiment includes treating the plants either prophylactically or after observance of infestation of the fire blight bacteria by applying a formulation for the control of the effects of the microorganism.

The application sequence when used as an aqueous formulation for the control of a plant pathogen such as fire blight includes applying a sufficient amount of the formulation to reduce the amount of damage done by the infection relative to plants similarly situated and not treated with the formulation. In one embodiment the ready-to-use spray formulation is applied in an amount sufficient to thoroughly wet or coat the leaves, flowers, stem, bark, trunk and the like without significant run off of the sprayed material. In one embodiment at least one additional application of the formulation may be made as necessary to control the pathogen.

For the purpose of promoting further understanding and appreciation of the present invention and its advantages, the following Examples are provided. It will be understood, however, that these Examples are illustrative and not limiting in any fashion.

EXAMPLE 1

Testing the Efficacy of Applying Beneficial Microorganisms and Nutrients Generally Applied to the Roots of a Plant to the Above Ground Structures of the Plant as a Method for Suppressing Fire Blight in Pear Trees A test plot was selected in east-central Indiana (U.S.A). The test plot included 17 rows of pear trees of differing species. The first 4 rows contained Cambridge pear trees. These trees had previously been exposed to *Erwinia amylovora*, the species of bacteria that causes fire blight. About 67% of the trees had been infected; about half of the infected trees died. The test plot included surviving trees adjacent to the infected dead trees. The next 2 rows were Autumn Blaze pear trees. These trees had about a 15% infection rate with a mortality rate of 8%. The next 7 rows were Aristocrat pear trees, a variety which is highly-susceptible to fire blight. The Aristocrat pear trees had about a 15% infection rate from the previous year. These trees were larger than the other trees in the test plot having trunks with an average diameter of about 3 to 4 inches. The final 4 rows included Cleveland Select pear trees; these trees had an infection rate of about 5%; none of these particular trees succumbed to the infection rate.

The plants in the test plot were divided into two groups. The first group (the control) was treated with a commercial product, MESSENGER® (sold by Eden Bioscience Corp., Bothell, Wash., USA). The active ingredient in MESSENGER® is Harpin protein. Harprin protein is thought to act against plant pathogens by inducing plants to activate their own protective mechanisms. About 9 ounces of MESSENGER® was mixed 100 gallons of water; plants in the control group were sprayed with this mixture.

The second group of trees was treated with a formulation comprising MESSENGER® and a fertilizer BIOPAK® Plus. According to its label, BIOPAK® Plus includes the beneficial bacteria *Rhizosphere Bacillus* in the amount of 5 billion colony forming units (cfu) per pound on a dry weight basis. It also has the same elemental analysis listed in Table 2. The same amount of MESSENGER® was added to this formulation as was added to the control, next 16 oz/100 gal of BIOPAK® Plus, was added to the formulation. A second group of trees were treated with this formulation.

All trees were treated at the first evidence of stamen development; at or about ⅓ of full bloom. A second application of both the control and the formulation was done at about ⅓ of full flower (15 days after the first application). The applications were made at these times because of the rate of fire blight infestation is highest during this stage of plant development.

The trees were observed on a regular basis after the application. Within 45 days after the initial application, the trees treated with the MESSENGER® only composition still exhibited the effects of fire blight. Many visibly diseased spores were visible; discoloration of leaves and cup-shaped leaves were readily apparent.

Figure 5:
FIG. 5 is a scanned image of a tree sprayed with a formulation for controlling fire blight.
Figure 6:
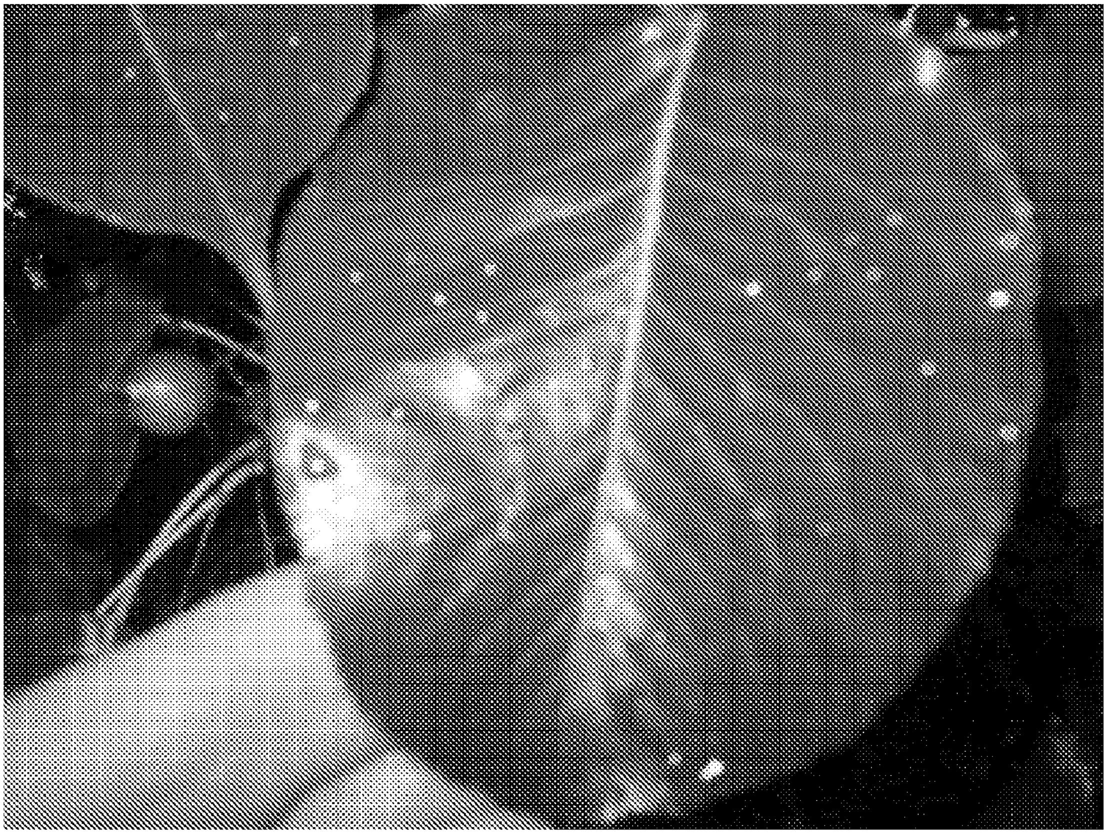
FIG. 6 is a scanned image of a leaf from a tree sprayed with a formulation for controlling fire blight.

Referring now to FIG. 5, a scanned image of a tree treated with a first application of MESSENGER®. Referring now to FIG. 6, a scanned image of a single leaf harvested from a tree previously infected with fire blight and then treated once with the formulation including the combination of MESSENGER® and BIOPAK® Plus.

No disease spores were visible on the surfaces of the trees treated with the MESSENGER® and BIOPAK® Plus combination. The new growth looked healthy it was free of contortions and had good color, development on the leaves and the stems (both old and new) appeared normal. New growth appeared on the previously infected trees and showed the same promising results as was observed for the uninfected trees.

Visual inspection of the trees was carried out 90 days after the first application of the formulation. The trees that were treated with the control continued to show evidence of fire blight infestation. Furthermore, the disease appeared to have spread among some of the previously uninfected trees of this group. Conversely the trees treated wit the formulation including both MESSENGER® and BIOPAK® Plus combination showed no signs of discoloration or other symptoms of an active fire blight infestation. Trees treated with the combination formulation exhibited new growth and good color below the regions of the trees killed by the previous fire blight infestation; no disease spores were detected in any of these trees.

Trees of the test plot were examined 120 days after the formulation was first applied. The trees treated with the control MESSENGER® only appeared to be significantly worse than at the beginning of the study these trees exhibited with evidence of further fire blight infestation and damage. The trees treated with the MESSENGER®/BIOPAK® Plus formulation still showed no physical signs of leaf or stem damage. These trees exhibited good color, bud development, and an increase in diameter on new growth shoots. The trees treated with the combination formulation appeared to exhibit an increase in disease resistance, flowering, plant respiration, cell division, photosynthesis, overall health and vigor; in short an increase in salability. The results from experiment 1 are summarized in Table 4. These results show that applying beneficial bacteria and nutrients generally applied to the soil to the above ground structures of a plant can help protect the plant from developing fire blight.

TABLE 1

| | | Biocidal Composition | | Average Growth (cm) | | | |
|---|---|---|---|---|---|---|---|
| Row | Pear Species | MESSENGER ® Only | MESSENGER ® and BIOPAK ® Plus | Internodal Length | Diameter | New Leaves Length | New Leaves Width |
| 1 | Cambridge | | X | 30.3 | 0.6 | 8 | 5 |
| 2 | Aristocrat | X | | 16 | 2.9 | 4 | 2.5 |
| 3 | Aristocrat | | X | 33 | 6 | 8 | 5 |
| 4 | Cleveland | | X | 37 | 5 | 6 | 4.5 |
| 5 | Select | | | | | | |
| 6 | Cleveland Select | X | | 28.8 | 3 | 4.5 | 5.5 |

EXAMPLE2

Formulation in Accordance with One Embodiment Useful for the Control of Plant Pathogens Including Fire Blight

TABLE 2

| Elemental Analysis | % by weight |
|---|---|
| 1. Total Nitrogen (N) | 3 |
| 2. Soluble Potassium ($K_2O$) | 20 |
| 3. Iron, Chelated (Fe) | 7 |
| 4. Sulfur (5) Combined | 4 |
| 5. Water Soluble Magnesium (Mg) | 1.5 |
| 6. Manganese, Chelated (Mn) | 0.2 |
| 7. Water Soluble Boron (B) | 0.02 |
| 8. Zinc, Chelated (Zn) | 0.2 |
| 9. Calcium glucoheptonate | 5 |
| 10. Beneficial Bacteria | 833 million cfu/lb |
| 11. Non-plant food ingredients | |

TABLE 3

| Listing of Beneficial Bacteria and Fungi | Million cfu/lb |
|---|---|
| 1. *Bacillus licheniformis* | 833 |
| 2. *Bacillus megaterium* | 833 |
| 3. *Bacillus polymyxa* | 833 |
| 4. *Bacillus subtilis* | 833 |
| 5. *Bacillus thuringiensis* | 833 |
| 6. *Paenibacillus azotofixans* | 833 |
| 7. *Streptomyces griseoviridis* | 1 |

TABLE 3-continued

| Listing of Beneficial Bacteria and Fungi | Million cfu/lb |
|---|---|
| 8. *Trichoderma harzianum* | 10 |
| 9. *Trichoderma konigii* | 10 |

TABLE 4

| Listing of Nutrients | % by weight |
|---|---|
| 1. Humic acids | 3.5 |
| 2. Cold Water Sea Kelp Extract | 4 |
| 3. Soluble Yucca Plant Extract | up to 12 |
| 4. Maltodextrin | up to 8 |
| 5. Sugar (Dextrose) | up to 12 |
| 6. Yeast | 5 |

EXAMPLE 3

A Preferred Formulation in Accordance with One Embodiment, Useful for the Control and Suppression of Plant Pathogens A formulation for the control or suppression of plant pathogens including fire blight was prepared including the compounds listed in Table 5. Whenever pome fruit trees such as Apple or Pear trees are treated *Tricoderma* and *Bacillus licheniformis* can be removed from the formulation.

This formulation and variations thereof were used to treat trees and shrubs in an orchard and nursery near Dayton, Ohio (USA). The results of these tests are described in the following Examples.

TABLE 5

Stock solution for direct application includes unless noted otherwise.
Unless otherwise noted to one hundred gallons of water was added the following:

| Amount | Description |
|---|---|
| 45 grams | dried inactive *Sacchromyces cervisiae* (yeast) |
| 45 grams | calcium glucoheptonate |
| ¼ pound | a mixture of microorganisms from Mycroohizal Application Inc., Grants Pass Oregon which includes: (1.1 Billion cfu per pound total) of *Rhizopogon rubescens*, *R. vulgaris*, *R. Subscaerlescens*, *R. ellanae*, *Pisolithus tinctorius*, *Laccaria laccata*, and *L. bicolor*, *Sceeroderma cepa* and *S. citrinum*. |
| 10 Billion cfu per pound | *Bacillus subtilis*, *Baccillus licheniformis*, *Bacillus axotoformans*, *Bacillus megaterium*, *Bacillus coagulans*, *Bacillus pumulis*, *Bacillus thurengiensis*, *Bacillus stearotermophilis*, *Paenbacillius polymyxa*, *Paenibaccillus durum*, *Azotobacter chroococcum*, *Azotobacter vinleandii*, *Sacchromyces cervisiae*, *Streptomyces lydicus*, *Pseudomonas aureofaceans* and *Pseudomonas fluorescens*, *Scleroderma cepa*, and *S. citrinum*. |

TABLE 5-continued

| Stock solution for direct application includes unless noted otherwise. Unless otherwise noted to one hundred gallons of water was added the following: | |
|---|---|
| Amount | Description |
| 3 Billion cfu per pound | *Tricoderma harzianum*, and *T. konigigii*. |
| 45 grams | yacca plant extract |
| 200 grams | agriplus humic acid at 212 microization |
| 181 grams | North Atlantic sea kelp and vitamin a package, which includes vitamins B, C and E. |

EXAMPLE 4

Evaluation of a Formulation Useful for the Suppression of Fire Blight in Pear Trees that are Susceptible to *E. amylovora*

Pear trees (*Pyrus*) that were exposed to *E. amylovora* the previous growing season, were treated with the formulation described in Example 3, minus the yacca plant extract and Kaolin clay.

A first spraying was preformed using a blast sprayer operated at a rate of about 200 gallons per hour. The trees were sprayed early in the growing seasoning during late morning, at a temperature of 52 degrees, relative humidity 37%, winds of less than 5 miles per hour, and cloudy skies. About 100 gallons per acre of the formulation was applied to a total of about 2.8 acres of Pear trees.

The tree in the test group were sprayed a second time proximately 9 days. The formulation used in the second spraying included both yacca extract as per the formulation in Example 3 and about 2.5 pounds per 100 gallons of water. Spray conditions for the second application were 64 degrees F., relative humidity of 67%, sunny, with a wind speed between 5 and 10 miles per hour.

All of the trees, both sprayed and unsprayed, were inspected approximately one month from the date of the first application. The trees sprayed with the formulation appeared healthy and were deemed to be in saleable condition. Trees in the sprayed rows showed no visible evidence of any new infection with fire blight. The trees, that were not sprayed with the formulation appeared droopy and were judged to be unsaleable.

EXAMPLE 6

Evaluation of a Formulation Useful for the Suppression of *Septoria* (leaf spot) in Dogwood Trees Susceptible to *Mycosphaerella populorum*

Dogwood trees in a test group were sprayed a first time with the formulation described in Example 3, which did not include either yacca plant extract or Kaolin clay. The first spraying was performed using a walking sprayer about 100 gallons per acre of the preparation was applied. The study included a total of forty-six (46) rows of trees covering a total of 1.9 acres. At the time of the first spraying in early may the temperature was about 62 degrees F. and the wind speed was about 5 miles per hour.

The same trees were sprayed a second time about two weeks after the first spraying. The formulation used in the second spraying included both yacca plant extract and about 2.5 pounds of Kaolin clay per 100 gallons of water. The temperature at the time of the second application was 71 degrees F., relative humidity was 70%, the winds were calm and the sky was cloudy.

Both sprayed and unsprayed trees were inspected about six weeks after the first spraying. Trees that were sprayed with the formulation showed little evidence of leaf spot.

EXAMPLE 7

Evaluation of a Formulation Useful for the Control of Cedar Hawthorn Rust in Hawthorn Trees Susceptible to *Gymnosporangium globovum*

A test group of Winter King Hawthorn trees were sprayed with the formulation described in Example 3, which did not include either yacca plant extract or Kaolin clay. Spraying was performed using a walking sprayer about 100 gallons per acre of the preparation was applied. The study included fifteen rows of trees covering at total of about 1.44 acres. At the time of the first spraying, in early May, the ambient temperature was 64 degrees F., the wind was 5-10 miles per hour, and conditions were sunny.

Both sprayed and unsprayed trees were evaluated about three weeks after the first spraying. The sprayed trees exhibit signs of an early, very light infection. The infection was allowed to develop. About one week after the three week inspection the trees were sprayed a second time. The formulation in the second spraying included both yacca plant extract and about 2.5 pounds of Kaolin clay per 100 gallons of water according the formulation described in Example 3.

All trees were inspected about six weeks after the first spraying the leaves and fruits on the Hawthorn trees that were sprayed were in much better condition than the leaves and fruits on the trees that were not sprayed. These results demonstrate that including compounds such a yacca plant extract and Kaolin clay extend the period of time over which this formulation remains effective.

EXAMPLE 8

Formulation Useful for the Control of Apple Scab in Crabapple Plants Susceptible to *Venturia inaequalis*

The ability of the formulation with and without Kaolin clay to control apple scab was tested on groups of Robinson, Sugartyme and Cardinal Crabapples trees. Trees in a test group were sprayed were sprayed with the formulation described in Example 3, which did not include either yacca plant extract or Kaolin clay. The temperature at the time of spraying was 65 degrees F., about 100 gallons of the formulation was applied per acre treated.

The trees were inspected about two weeks after the first spraying. All trees exhibited filaments on their petioles. Four days after the first inspection trees in the test group were sprayed a second time with a formulation that included both yacca plant extract according to the formulation in Example 4 and about 2.5 pounds of Kaolin clay per 100 gallons of water.

All trees were inspected two week after the second spraying. The sprayed trees were free of any evidence of apple scab infestation including filaments on or near the petioles and or on the leaves. The result demonstrate the utility of adding clay and yacca plant extract to the formulation and the overall usefulness of the formulation in the control of *V. inaequalis* on Crabapple Trees.

EXAMPLE 9

Formulation Useful for the Suppression of Fire Blight in Pear Trees Susceptible to *E. amylovora*

A test group of *Pyrus* (Pear) Aristocrat and *Pyrus* Autumn Blaze trees that were exposed to Fire Blight in the previous growing season were sprayed with the formulation prepared in accordance with the formulation described in Example 3. The formulation used in the first spraying did not include either yacca plant extract or Kaolin clay. Trees in the test group were sprayed during early to full bloom. At the time of the first spraying the temperature was 70 F, about 100 gallons of the formulation was applied per acre.

The sprayed plants were inspected biweekly and they showed no evidence of fire blight for about 4 weeks. After four weeks signs of fire blight were detected. The trees were then sprayed a second time. The formulation used in the second spraying included both yacca plant extract according to the formulation in Example 3 and about 2.5 pounds of Kaolin clay per 100 gallons of water. The trees were inspected two weeks after the second spraying and showed no change.

Having now been sprayed with a formulation including both yacca and clay it is expected that the treated trees will show less overall damage and mortality than the trees that were not sprayed with the formulation.

EXAMPLE 10

Forumulation Useful for the Suppression of Birch Rust in Birch Trees Susceptible to *Gnomonia setecea*

A test group of Birch trees were sprayed with the formulation prepared in accordance with the formulation described in Example 3. The formulation used in the first spraying did not include either yacca plant extract or Kaolin clay. Trees in the test group were sprayed during early to full bloom using a Blast Sprayer. At the time of the first spraying the temperature was 71 F; about 50 gallons per acre of the formulation was applied to a total of about 1.95 acres.

The trees were inspected about 4 weeks after the first spraying. No evidence of Birch Blight was found in either the treated or untreated groups of trees. All trees showed some spotting and yellowing, but this was attributed to a soil nutrient deficiency not a pathogen infestation.

EXAMPLE 11

Formulation Useful for the Suppression of Apple Scab in Crabapple Trees Susceptible to *V. inaequalis*

A test group of Prairie Fire and Snowdrift Crabapple trees were sprayed with the formulation prepared in accordance with the formulation described in Example 3. The formulation used in the first spraying did not include either yacca plant extract or Kaolin clay. Trees in the test group were sprayed during early to full bloom using a Blast Sprayer. At the time of the first spraying the temperature was 58 degrees F., the relative humidity was about 50 per cent the wind speed was about 13 mph under cloudy skies. About 100 gallons per acre of the formulation was applied to about 24 rows of trees located on 4.26 acres of land.

The trees were sprayed a second time about four weeks after the first spraying. The formulation used in the second spraying included both yacca plant extract according to the formulation in Example 3 and about 2.5 pounds of Kaolin clay per 100 gallons of water.

The sprayed trees looked better than the trees in the control group which were not sprayed, although even the sprayed trees showed light to medium scab development.

In light of this second spraying which included Kaolin clay and yacca plant extract it is likely, that the sprayed trees will show less damage and mortality than the trees that were not sprayed.

EXAMPLE 12

Formulation Useful for the Suppression of Juniper Blight in Juniper Shrubs Susceptible to *Kabatuna juniperii*

A test group of Juniper shrubs were sprayed with the formulation prepared in accordance with the formulation described in Example 3. The formulation used in the first spraying included yacca plant extract in accordance with the formulation described in Example 4 and 2.5 pounds of Kaolin clay per 100 gallons of water. Trees in the test group were sprayed using a walking sprayer. Conditions at the time of the first spraying were: temperature 71 degrees F., winds calm and skies cloudy.

Two rows, one of about 1.74 acres and a second row of about 2.75 acres were spayed. About 50 gallons per acre of the formulation was applied. The trees were inspected in early July, about three weeks after the formulation was applied, none of the sprayed trees showed any evidence of Juniper Blight.

All references, patents, patent application and the like cited herein and not otherwise specifically incorporated by references in their entirety, are hereby incorporated by references in their entirety as if each were separately incorporated by reference in their entirety.

An abstract is included in to aid in searching the contents of the abstract are not intended to be read as explaining, summarizing or otherwise characterizing or limiting the invention in any way.

While the invention has been illustrated and described in detail, this is to be considered as illustrative, and not restrictive of the patent rights. The reader should understand that only the preferred embodiments have been presented and all changes and modifications that come within the spirit of the invention are included if the following claims or the legal equivalent of these claims.

The present invention contemplates modifications as would occur to those skilled in the art. It is also contemplated that processes embodied in the present invention can be altered, duplicated, combined, or added to other processes as would occur to those skilled in the art without departing from the spirit of the present invention.

Unless specifically identified to the contrary, all terms used herein are used to include their normal and customary terminology.

Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. A formulation for controlling plants pathogens, comprising:

a) a microbe mixture comprising *Bacillus subtilis, Baccillus licheniformis, Bacillus axotoformans, Bacillus megaterium, Bacillus coagulans, Bacillus pumulis, Bacillus thurengiensis, Bacillus stearotermophilis, Paenbacillius polymyxa, Paenibaccillus durum, Azotobacter chroococcum, Pseudomonas aureofaceans*, and *Pseudomonas fluorescens*;

b) Kaolin clay;

c) a yeast;

d) a Yucca plant extract; and e) a calcium salt.

2. The formulation according to claim 1, wherein said formulation is dispersed in an aqueous preparation and includes between 1.5 and 10 pounds of Kaolin clay per 100 gallons of aqueous preparation.

3. A formulation according to claim 1 wherein said calcium salt comprises calcium glucoheptonate.

4. A method for controlling plant pathogens selected from the group consisting of *Erwinia amylovora, Venturia inaequalis, Gnomonia setecea, Mycosphaerella populorum, Gymnosporangium* and *Kabatina juniperii*, comprising the steps of:

providing a formulation comprising:

a) a microbe mixture comprising *Bacillus subtilis, Baccillus licheniformis, Bacillus axotoformans, Bacillus megaterium Bacillus coagulans Bacillus umulis Bacillus thuren iensis Bacillus stearotermophilis, Paenbacillius polvmvxa, Paenibaccillus durum, Azotobacter chroococcum, Pseudomonas aureofaceans*, and *Pseudomonas fluorescens;* b) Kaolin clay;

c) a yeast;

d) a Yucca plant extract; and e) a calcium salt; and applying said formulation to at least one surface of a plant.

5. The method according to claim 4, wherein said applying step is selected from the group consisting of, spraying, dusting, and drenching said plant with said formulation.

6. The method according to claim 4, wherein said plant is susceptible to infection with at least one type of blight selected from the group consisting of fire blight, Birch Blight, Juniper Blight, Cedar Hawthorn Rust, Apple Scab and Leaf Spot.

* * * * *